US011000833B2

(12) United States Patent
Werner

(10) Patent No.: US 11,000,833 B2
(45) Date of Patent: May 11, 2021

(54) TABLETED CATALYST FOR METHANOL SYNTHESIS HAVING INCREASED MECHANICAL STABILITY

(71) Applicant: CLARIANT INTERNATIONAL LTD, Muttenz (CH)

(72) Inventor: Sebastian Werner, Vaterstetten (DE)

(73) Assignee: Clariant International Ltd, Muttenz (CH)

( * ) Notice: Subject to any disclaimer, the term of this patent is extended or adjusted under 35 U.S.C. 154(b) by 31 days.

(21) Appl. No.: 16/463,551

(22) PCT Filed: Dec. 14, 2017

(86) PCT No.: PCT/EP2017/082815
§ 371 (c)(1),
(2) Date: May 23, 2019

(87) PCT Pub. No.: WO2018/109083
PCT Pub. Date: Jun. 21, 2018

(65) Prior Publication Data
US 2020/0001278 A1    Jan. 2, 2020

(30) Foreign Application Priority Data

Dec. 15, 2016  (DE) .......................... 102016225171.6

(51) Int. Cl.
| | | |
|---|---|---|
| *B01J 23/80* | (2006.01) | |
| *B01J 23/00* | (2006.01) | |
| *B01J 35/00* | (2006.01) | |
| *B01J 35/02* | (2006.01) | |
| *B01J 35/10* | (2006.01) | |
| *B01J 37/00* | (2006.01) | |
| *B01J 37/08* | (2006.01) | |
| *B01J 37/18* | (2006.01) | |
| *C07C 29/154* | (2006.01) | |

(52) U.S. Cl.
CPC ............. *B01J 23/80* (2013.01); *B01J 23/002* (2013.01); *B01J 35/0053* (2013.01); *B01J 35/026* (2013.01); *B01J 35/1014* (2013.01); *B01J 35/1019* (2013.01); *B01J 35/1038* (2013.01); *B01J 37/0018* (2013.01); *B01J 37/08* (2013.01); *B01J 37/18* (2013.01); *C07C 29/154* (2013.01); *B01J 2523/17* (2013.01); *B01J 2523/27* (2013.01); *B01J 2523/31* (2013.01)

(58) Field of Classification Search
None
See application file for complete search history.

(56) References Cited

U.S. PATENT DOCUMENTS

| | | |
|---|---|---|
| 3,923,694 A | 12/1975 | Cornthwaite |
| 4,111,847 A | 9/1978 | Stiles |
| 4,126,581 A | 11/1978 | Sugier |
| 4,535,071 A | 8/1985 | Schneider |
| 4,871,710 A | 10/1989 | Denny |
| 5,387,408 A | 2/1995 | Schneider |
| 6,020,285 A | 2/2000 | Hancock |
| 6,261,465 B1 | 7/2001 | Hancock |
| 7,084,312 B1 | 8/2006 | Huber |
| 7,754,651 B2 | 7/2010 | Ladebeck |
| 7,884,046 B2 | 2/2011 | Huber-Dirr |

FOREIGN PATENT DOCUMENTS

| | | |
|---|---|---|
| FR | 2106636 | 5/1972 |
| RU | 2172210 | 8/2001 |
| WO | 03053575 | 7/2003 |
| WO | 2005087374 | 9/2005 |
| WO | 2013072197 | 5/2013 |

OTHER PUBLICATIONS

V.I Yakerson "Design of Heterogeneous Catalyic Systems . . . " React. Kinet. Catal. Lett. 55(2), 1995, 455-462.
V.I Yakerson "Scientific bases for the preparation of new cement containing catalysts" Preparation of Catalysts VI, Scientific Bases for the Preparation of Heterogeneous Catalysts 1995, 879, Textbook.
Valentin Antonovic "The Effect of Temperature on the Formation of the Hydrated . . . " Procedia Engineering 57(2013), 99-106.

*Primary Examiner* — Colin W. Slifka

(57) ABSTRACT

The invention relates to an improved catalyst based on a tableted molded catalyst body, containing a metal-containing mixture, containing copper, zinc, and aluminum, with calcium aluminate as a binder material with a weight fraction of calcium aluminate in the range of 1.0% to 30.0%, for synthesizing methanol from synthesis gas. The invention further relates to the production of the catalyst and to the use of the catalyst in the synthesis of methanol from synthesis gas.

19 Claims, No Drawings

TABLETED CATALYST FOR METHANOL SYNTHESIS HAVING INCREASED MECHANICAL STABILITY

The present invention relates to an improved catalyst based on a tableted shaped catalyst body containing copper, zinc and aluminum with calcium aluminate as binder material for the synthesis of methanol from synthesis gas, characterized in that the shaped catalyst body comprises a proportion by weight of calcium aluminate in an amount of from 1.0 to 30.0% based on the shaped catalyst body. The present invention additionally relates to the production of the catalyst and the use thereof in the synthesis of methanol from synthesis gas.

BACKGROUND OF THE INVENTION

Catalytic processes for the synthesis of methanol have great relevance in industry. With an annual consumption of more than 80 million t, methanol is among the most important industrial chemicals and intermediates. On an industrial scale, the synthesis of methanol usually proceeds from a synthesis gas consisting of CO, $CO_2$ and $H_2$ at elevated pressure and elevated temperature.

Suitable catalysts here are systems based on copper and zinc. These are usually present in the form of tablets, extrudates or granules.

WO 2004/085356 describes the production of a catalyst for the hydrogenation of carbonyl compounds, which contains at least one oxide of lanthanum, tungsten, molybdenum, titanium or zirconium in addition to copper and aluminum and into which copper powder or flakes, cement powder or graphite has also been mixed.

U.S. Pat. No. 6,020,285 describes the production of a cobalt- or nickel-containing catalyst which additionally comprises calcium aluminate having an Al/Ca ratio of greater than 2.5. The catalyst is suitable for the decomposition of hypochlorite.

WO 98/11985 discloses cobalt- or nickel-containing catalysts which further comprise calcium aluminate having an Al/Ca ratio of greater than 4.0 and also alumina and/or magnesia. The catalyst is suitable for the decomposition of oxidizing substances.

U.S. Pat. No. 7,084,312 describes the production of catalysts based on copper, zinc and aluminum, for which an oxidic mixture of copper, zinc and aluminum is mixed with metallic copper, a cement or a mixture of the two materials and shaped to give tablets. The catalyst is used for hydrogenating organic compounds bearing carbonyl groups.

Yakerson et al. (Scientific Bases for the Preparation of Heterogeneous Catalysts, Preparation of Catalysts, p. 879 ff.) describe the production of cement-containing metal catalysts, for example nickel-, copper- or zinc-containing catalysts. The corresponding metal hydroxocarbonates are used for this purpose.

The filling of reactors for the synthesis of methanol is carried out on an industrial scale by charging the reactor with the shaped catalyst bodies from the upper end of the reactor. As a result, the shaped catalyst bodies experience severe mechanical stress on impingement on the bottom, which sometimes leads to individual shaped catalyst bodies breaking or individual constituents being rubbed off. This leads to partial blockage of the reactor and a significant increase in the pressure drop during synthesis operation. This is associated with a considerably increased energy consumption for the compressors and thus higher operating costs. Furthermore, the increased pressure drop results in greater mechanical stressing of the reactor which goes as far as the design limit of the latter, i.e. a pressure increase to which the reactor can be subjected without damage, e.g. to the reactor walls. This has the consequence that the volume flow in the plant has to be reduced or plant operation has to be interrupted in order to carry out renewed filling. Both results in a considerable decrease in production output, which impairs the economics of the process.

Apart from a fracture strength in the oxidic form, which is of importance for charging of the reactor, the shaped catalyst body also has to have a sufficient compressive strength in its reduced form in which it is present under the reaction conditions of the synthesis of methanol in order to withstand the mechanical stress brought about by the total weight of the catalyst bed in the process reactor. The shaped catalyst body is subjected to further mechanical stresses by the intrinsic weight of the catalyst bed and by the process pressure during the process of methanol synthesis. A lower mechanical stability of the catalyst in its reduced form leads to the proportion of particles from broken shaped bodies increasing over time and leads to a further increase in the pressure drop and a possible decrease in the catalytic activity.

It is therefore an object of the present invention to provide a catalyst for the synthesis of methanol which displays an improved mechanical fracture strength and lateral compressive strength, particularly in the reduced state.

This object is achieved by the catalyst of the invention.

DESCRIPTION OF THE INVENTION

The invention provides a shaped catalyst body in tablet form containing a metal-containing mixture containing copper, zinc and aluminum and calcium aluminate as binder material with a proportion by weight of calcium aluminate in the range from 1.0% to 30.0%, based on the shaped catalyst body, and also the production thereof and use thereof as catalyst in the synthesis of methanol.

The shaped catalyst body of the invention is produced by means of the following steps according to the invention:
 a) mixing of a metal-containing mixture containing copper, zinc and aluminum with calcium aluminate and a lubricant and optionally water,
 b) tableting of the mixture from step a) to give a tableted shaped body,
 c) thermal treatment of the tableted shaped bodies at a temperature between 100 and 500° C. for a time between 30 minutes and 4 hours.

The proportion by weight of calcium aluminate in the shaped catalyst body after step c) is in the range from 1.0% to 30.0%, preferably in the range from 5.0% to 20.0%, more preferably in the range from 10.0 to 15.0%.

The metal-containing mixture containing copper, zinc and aluminum which is used in step a) can be selected from the group of oxides, hydroxides or carbonates. Preference is here given to the oxides of the corresponding elements. The elements can be present either as individual compounds such as copper oxide, zinc oxide or aluminum oxide or as mixed compounds such as mixed oxides of copper, zinc and aluminum.

The metal-containing mixture used in step a) can be obtained by precipitation of the dissolved metal ions from aqueous solution. Suitable starting compounds are in principle all compounds which are soluble in water or basic or acidic aqueous solutions. Preference is given to using nitrates, halides, oxides, sulfates, acetates or formates. Aluminum can also be present as aluminate.

The metal-containing mixture used in step a) can preferably be subjected beforehand to a thermal treatment. The temperature here is preferably from 200 to 500° C., more preferably from 250 to 400° C., most preferably from 300 to 400° C.

The mixture obtained after step a) contains the metal-containing mixture, calcium aluminate and a lubricant. Water can optionally also be added in step a), so that the mixture after step a) also contains water. When water is added in step a), this is added in a proportion of from 0.5 to 20.0% by weight, preferably from 1.0 to 15.0% by weight and particularly preferably from 5.0 to 10.0% by weight, based on the dry mass of the mixture from step a).

When water is added in step a), the mixture obtained after step a) can optionally then be subjected to an aging step. Here, the mixture is stored for from 5 minutes to 3 hours without further components being added or the mixture being kept in motion. The aging temperature usually corresponds to the temperature of the surroundings of the mixture, but can be set in a controlled manner within a range from 0° C. to 90° C.

The mixture obtained after step a), which has optionally also been aged, is subsequently usually optionally compacted and/or granulated without a thermal treatment and is then subjected to a tableting step b). Commercial tableting machines, for example of the type Pressima from IMA Kilian, are used here. The tableting pressure employed here is usually in the range from 10 N/mm² upward. The mixture after step a) contains a lubricant. This is a compound which assists the tableting properties of the mixture. Suitable lubricants are graphite, oils or stearates, preferably graphite. The lubricant is preferably added in a proportion of from 0.1 to 5.0% by weight, more preferably from 0.5 to 5.0% by weight, and particularly preferably from 1.0 to 4.0% by weight, to the composition to be tableted.

The thermal treatment of the tablets is carried out at a temperature between 100 and 500° C., preferably between 150 and 400° C. The duration of this thermal treatment is between 30 minutes and 4 hours, preferably between 1 and 3 hours and particularly preferably 2 hours.

The atomic ratio of copper to zinc in the metal-containing mixture from step a) can vary within wide limits, but is preferably matched to that of conventional catalysts for the synthesis of methanol. The atomic ratio of copper to zinc in the metal-containing mixture from step a) is between 4 and 1, preferably between 3.0 and 2.0 and particularly preferably between 2.5 and 2.2. The atomic ratio of copper to aluminum in the metal-containing mixture from step a) is between 7.0 and 3.0, preferably between 6.0 and 3.5, and particularly preferably between 5.2 and 3.8. The atomic ratio of zinc to aluminum in the metal-containing mixture from step a) is between 4.0 and 0.5, preferably between 2.8 and 1.3 and particularly preferably between 2.2 and 1.5.

The calcium aluminate is a compound containing Ca and Al in the form of oxides and/or hydroxides. It can be, for example, composed of calcined calcium aluminates of the general formula x CaO.y Al2O3 or chemically precipitated calcium aluminates of the general formula $Ca_aAl_b(OH)_c$. Depending on the treatment of the calcium aluminates, however, intermediate stages between these two empirical formulae can also be present, and these are likewise suitable as binder material. Apart from these elements, further elements can be present in the calcium aluminate. In a preferred embodiment, the calcium aluminate contains further elements in a proportion by weight of less than 5.0% by weight, preferably less than 1.0% by weight and particularly preferably less than 0.1% by weight, based on the weight of the calcium aluminate.

The atomic Ca/Al ratio of the calcium aluminate which is used in the present invention can vary and is preferably between 0.9 and 3.5, even more preferably between 1.0 and 2.0. Synthetically produced materials are suitable as calcium aluminates. However, it is also possible to use naturally occurring calcium aluminates, e.g. katoite.

The tableted shaped catalyst body can have various dimensions. The diameter of the tablets can be between 2 and 8 mm and preferably between 4 and 7 mm. The diameter is particularly preferably 6 mm. The height of the tablets can be between 2 and 6 mm and preferably between 3 and 5 mm. The height is particularly preferably 4 mm.

The calcium aluminate can be subjected to a thermal treatment (calcination) before use as binder material. This thermal treatment takes place at a temperature between 100 and 500° C., preferably between 150 and 400° C. and particularly preferably between 200 and 300° C.

In one embodiment of the invention, the particles of the calcium aluminate have an average particle size having a $d_{50}$ in the range from 0.5 to 150 μm, measured by the laser light scattering method (low angle laser light scattering), e.g. using the Malvern Mastersizer 2000.

The atomic ratio of copper to zinc in the shaped catalyst body of the invention can vary within wide limits, but is preferably matched to that of conventional catalysts for the synthesis of methanol. The atomic Cu/Zn ratio in the shaped catalyst body is between 4 and 1, preferably between 3.0 and 2.0, and particularly preferably between 2.5 and 2.2.

The catalysts in tablet form which are produced by the process of the invention have a lateral compressive strength of from 50 to 300 N, preferably from 100 to 250 N, particularly preferably from 150 to 250 N, in the oxidic state. The tablets produced by tableting preferably have a diameter in the range from 5 to 7 mm, a height in the range from 3 to 5 mm and a lateral compressive strength in the range from 160 to 220 N.

In a further embodiment, the tableted shaped bodies obtained in step (c) are reduced in a subsequent step (d).

The reduction is preferably carried out by heating the tableted shaped catalyst body in a reducing atmosphere. For example, the reducing atmosphere is hydrogen. The hydrogen is preferably mixed with an inert gas, for example nitrogen. The proportion of hydrogen in the hydrogen/nitrogen mixture is typically in the range from 1 to 4% by volume. The reduction is, for example, carried out at a temperature in the range from 150° C. to 450° C., in particular in the range from 180° C. to 300° C., preferably in the range from 190° C. to 290° C., particularly preferably at about 250° C.

The reduction is, for example, carried out as a function of the amount of catalyst to be reduced over a period of from 1 hour (in the case of, for example, 500 g) to 10 days (in the case of, for example, 100 metric tons), in particular over a period of from 2 hours to 120 hours, preferably over a period of from 24 to 48 hours. Amounts of catalyst on the production scale (for example in the range from 1 to 60 metric tons) are preferably reduced over a period of from 3 to 8 days.

In a preferred embodiment, the shaped catalyst bodies are stabilized either wet or dry after reduction. In the case of wet stabilization, the shaped catalyst bodies are covered with a liquid in order to avoid contact with oxygen as far as possible. Suitable liquids encompass organic liquids and water, preferably organic liquids. Preferred organic liquids are those which at 20° C. have a vapor pressure of 0.5 hPa or less. Examples of such suitable organic liquids are isodecanol, Nafol, fatty alcohols, hexadecane, 2-ethylhexanol, propylene glycol and mixtures thereof, in particular isodecanol.

In the case of dry stabilization, a mixture of oxygen or an oxygen-containing gas, preferably air, and an inert gas such as argon or nitrogen is introduced into the reduction space. The concentration of oxygen in the mixture is preferably increased from about 0.04% by volume to about 21% by volume. For example, a mixture of air and inert gas can be introduced, with the ratio of air to inert gas initially being about 0.2% by volume of air to 99.8% by volume of inert gas. The ratio of air to inert gas is then gradually increased (e.g. continuously or stepwise) until finally, for example, 100% by volume of air is introduced (corresponding to an oxygen concentration of about 21% by volume). Without wishing to be tied to a theory, it is presumed that a thin oxide layer having a thickness of, for example, from 0.5 to 50 nm, preferably from 1 to 20 nm, particularly preferably from 1 to 10 nm, is formed on the surface of the catalyst as a result of the introduction of air or oxygen and protects the shaped catalyst body against further oxidation. In dry stabilization, the reactor temperature is preferably 100° C. or less, particularly preferably from 20° C. to 70° C. and most preferably from 30° C. to 50° C. The reduction can be carried out ex situ or in situ in the reaction plant into which the shaped catalyst body is introduced as catalyst.

After treatment under reducing conditions and subsequent dry stabilization, the tablets have a lateral compressive strength of from 40 to 200 N, preferably from 40 to 100 N, more preferably from 50 to 100 N, particularly preferably from 50 to 80 N.

The shaped catalyst body of the invention is characterized in that it contains calcium aluminate in a proportion by weight of from 1.0% to 30.0%, based on the shaped catalyst body. The proportion is preferably from 5.0% to 20.0% and particularly preferably from 8.0% to 12.0%.

The active copper surface area of the reduced shaped catalyst body is between 20 $m^2/g$ and 50 $m^2/g$, preferably between 20 $m^2/g$ and 40 $m^2/g$, particularly preferably between 25 $m^2/g$ and 36 $m^2/g$.

The catalyst obtainable by means of the process of the invention preferably has a BET surface area in the range from 70 to 150 $m^2/g$, in particular from 75 to 140 $m^2/g$ and particularly preferably from 80 to 120 $m^2/g$.

The pore volume of the shaped catalyst body of the invention, measured by means of mercury porosimetry, is between 150 $mm^3/g$ and 400 $mm^3/g$, preferably between 250 $mm^3/g$ and 350 $mm^3/g$, particularly preferably between 300 and 350 $mm^3/g$.

The proportion of the pore volume made up by pores having a radius of from 7.0 to 40.0 nm in the shaped catalyst body of the invention is preferably between 50 and 95%, preferably between 80 and 90%, of the total pore volume.

The invention additionally provides for the use of the shaped catalyst body of the invention in the synthesis of methanol from synthesis gas. For the purposes of the present invention, synthesis gas is a gaseous composition containing CO, $CO_2$ and $H_2$. The synthesis gas is usually composed of from 5 to 25% by volume of CO, from 6 to 12% by volume of $CO_2$, from 10 to 30% by volume of at least one gas which is inert under the reaction conditions, e.g. nitrogen and/or methane together, with the remainder of the gas composition being $H_2$.

Usual reaction temperatures in the synthesis of methanol are between 200 and 300° C., preferably between 210 and 280° C., and the pressure is usually in the range from 40 to 150 bar, preferably from 60 to 100 bar, and the space velocity of the gas composition is in the range from 2000 to 22 000 $h^{-1}$. The space velocity here is the ratio of the volume flow of the synthesis gas to the three-dimensional volume of the catalyst, in the case of a catalyst bed the bulk volume of this bed, per hour.

EXAMPLES

The determinations of the loss on ignition in the context of the present invention were carried out by determining the weight of about 1-2 g of a sample of the material to be analyzed, subsequently heating the sample to 900° C. under a room atmosphere and maintaining it at this temperature for 3 hours. The sample was subsequently cooled under a protective atmosphere and the residual weight was measured. The difference between the weight before and after the thermal treatment corresponds to the loss on ignition.

The determination of the lateral compressive strength was carried out in accordance with DIN EN 1094-5. Here, a statistically significant number of tablets (at least 40 tablets) were measured and the arithmetic mean of the individual measurements was calculated. This mean corresponds to the lateral compressive strength of a particular sample.

To determine the lateral compressive strength of the reduced and dry-stabilized shaped catalyst body, a particular amount was heated under reducing gas (2% by volume of $H_2$ in $N_2$) to 200° C. and reduced at this temperature for 24 hours. The material was cooled to room temperature under a stream of nitrogen. Synthetic air was then introduced into the stream of nitrogen and the material was passivated in this way. The lateral compressive strength of the samples which have been treated in this way was then determined as described in the previous paragraph.

The determination of the fracture strength was carried out by allowing 100 g of the tablets according to the invention to fall through a vertical steel tube having a diameter of 60 mm and a length of 3 m. After passing through the steel tube, the tablets were collected in a glass beaker. An optical assessment was subsequently employed to determine the proportion of the tablets which have survived falling without spalling, formation of broken edges or other deviations from the original cylindrical shape. The proportion of fractured tablets can be determined as difference between the tablets used and the tablets which have survived falling without spalling, formation of broken edges or other deviations from the original cylindrical shape, divided by the weight of the tablets used.

The specific BET surface areas were determined by means of nitrogen adsorption in accordance with DIN 66131.

The pore volume of the shaped catalyst body was measured by the mercury porosimetry method in accordance with DIN 66133.

The proportion by weight of calcium aluminate in the shaped catalyst body could be determined by means of X-ray diffraction. For this purpose, the sample was measured over a range from 5 to 90 2° Θ (steps of 0.020 2° Θ, 1.5 seconds measurement time per step). CuKα radiation was used. The spectrum of intensities of reflections obtained was quantitatively analyzed by means of Rietveld refinement and the proportion of calcium aluminate in the sample was determined. To determine the proportion of the respective crystal phases, the software TOPAS from BRUKER was used.

The Cu surface area was determined by firstly grinding a shaped catalyst body in a mortar and introducing about 100 mg of the 100-250 μm sieve fraction into a fused silica reactor. The catalyst was subsequently reduced/activated as described above at atmospheric pressure. After conclusion of the reduction, the catalyst was brought to 35° C. under He. A calibrated mass spectrometer configured for detecting $N_2O$ and $N_2$ was located in the offgas stream from the reactor. A volume flow of 7.5 sccm of 1% $N_2O$ in He was subsequently fed in and the outflowing gas stream was analyzed. The reaction of elemental copper with $N_2O$ at the Cu surface formed oxidized $Cu_2O$ and $N_2$. The consumption of $N_2O$ in mole could be determined by integration of the signal area of the $N_2$ present in the volume flow exiting from the reactor and the calibrated flow of $N_2O$/He. Assuming a specific copper surface area of $1.47 \cdot 10^{19}$ atoms of $Cu/m^2$, the surface area could be calculated; the Cu surface area is thus given by the ratio of surface area to weight of sample.

Production of the Catalyst Powder

To produce the catalysts, a 14% strength by weight aqueous sodium carbonate solution was prepared and heated to 50° C. In a second vessel, 820 g of copper nitrate, 120 g of zinc oxide and 260 g of aluminum nitrate were dissolved at 50° C. in 900 g of water and 270 g of 68% strength by weight $HNO_3$. The nitrate solution and the sodium carbonate solution were simultaneously combined at a temperature of 65° C. while keeping the pH constant at 6.5 (precipitation). The suspension was pumped continuously from the precipitation vessel into an aging vessel. After the precipitation was complete, the suspension was aged at 70° C. for at least 120 minutes. The color changed from light blue (beginning of aging) to green (end of aging). After aging, the suspension was filtered and the filter cake was washed until the sodium content of the filter cake, determined by atomic absorption spectroscopy, was less than 350 ppm. The filter cake was slurried by addition of water and dried in a spray dryer at an inlet temperature of from 270° C. to 275° C. and an outlet temperature of from 105° C. to 115° C. to give a solid catalyst precursor. The solid catalyst precursor obtained was used for producing the shaped catalyst bodies described below.

For the analytical determination of the composition, part of the solid catalyst precursor was thermally treated at 330° C. for 2 hours. The chemical composition was (figures in % by weight): 64.0% of CuO, 27.8% of ZnO, 8.2% of $Al_2O_3$, based on the total mass after loss on ignition. This corresponds to an empirical formula of $CuZn_{0.425}Al_{0.2}O_{1.725}$.

The dried powder was subsequently thermally treated at 320° C. for 2 hours and served as starting material for the tableting examples.

Comparative Example 1 (Comparative Catalyst)

The comparative catalyst A was produced by mixing 500 g of the catalyst powder with 2 g of graphite and subsequently shaping the mixture to give tablets having dimensions of 6 mm in diameter and 4 mm in height.

Example 1 (Catalyst 1)

500 g of the catalyst powder were mixed with 50 g of calcium aluminate (SECAR 71, 30% by weight of CaO, 70% by weight of $Al_2O_3$) and 10 g of graphite. The mixture was subsequently shaped to give tablets having dimensions of 6 mm in diameter and 4 mm in height. The sample which had been tableted in this way was not subjected to any thermal treatment. The lateral compressive strength was determined on the tablet sample produced in this way and also on the subsequently reduced and dry-stabilized sample.

Example 2 (Catalyst 2)

500 g of the catalyst powder were mixed with 50 g of calcium aluminate (SECAR 71, 30% by weight of CaO, 70% by weight of $Al_2O_3$) and 10 g of graphite. The mixture was subsequently shaped to give tablets having dimensions of 6 mm in diameter and 4 mm in height. The sample which had been tableted in this way was subsequently thermally treated at 400° C. for 2 hours. The lateral compressive strength was determined on the tablet sample produced in this way and also on the subsequently reduced and dry-stabilized sample.

Example 3 (Catalyst 3)

500 g of the catalyst powder were mixed with 62.5 g of calcium aluminate (SECAR 71, 30% by weight of CaO, 70% by weight of $Al_2O_3$) and 10 g of graphite. The mixture was subsequently shaped to give tablets having dimensions of 6 mm in diameter and 4 mm in height. The sample which had been tableted in this way was subsequently thermally treated at 400° C. for 2 hours. The lateral compressive strength was determined on the tablet sample produced in this way and also on the subsequently reduced and dry-stabilized sample.

Example 4 (Catalyst 4)

500 g of the catalyst powder were mixed with 100 g of calcium aluminate (SECAR 71, 30% by weight of CaO, 70% by weight of $Al_2O_3$) and 10 g of graphite. The mixture was subsequently shaped to give tablets having dimensions of 6 mm in diameter and 4 mm in height. The sample which had been tableted in this way was subsequently thermally treated at 400° C. for 2 hours. The lateral compressive strength was determined on the tablet sample produced in this way and also on the subsequently reduced and dry-stabilized sample.

| Example | Weight ratio of calcium aluminate/catalyst powder [%] | Temperature of the thermal treatment [° C.] | Lateral compressive strength before reduction and dry stabilization [N] | Lateral compressive strength after reduction and dry stabilization [N] | Proportion of broken material [% by weight] | Cu surface area [$m^2$/g] | Pore volume [$mm^3$/g] | BET surface area [$m^2$/g] |
|---|---|---|---|---|---|---|---|---|
| Comparative catalyst | — | no thermal treatment | 191 | 33 | 16.6 | 36 | 286 | 104 |
| Catalyst 1 | 10.0 | no thermal treatment | 196 | 30 | 5.5 | 36 | 330 | 126 |

-continued

| Example | Weight ratio of calcium aluminate/catalyst powder [%] | Temperature of the thermal treatment [° C.] | Lateral compressive strength before reduction and dry stabilization [N] | Lateral compressive strength after reduction and dry stabilization [N] | Proportion of broken material [% by weight] | Cu surface area [m$^2$/g] | Pore volume [mm$^3$/g] | BET surface area [m$^2$/g] |
|---|---|---|---|---|---|---|---|---|
| Catalyst 2 | 10.0 | 400 | 229 | 77 | 7.9 | 34 | 363 | 115 |
| Catalyst 3 | 12.5 | 400 | 155 | 84 | 8.2 | 25 | 381 | 81 |
| Catalyst 4 | 20 | 400 | 115 | 91 | 8.6 | 22 | 331 | 75 |

It can clearly be seen from table 1 that the catalysts according to the invention have a significantly improved fracture strength. In addition, those shaped bodies which were subjected to a subsequent thermal treatment of the tablets also have a significantly increased lateral compressive strength after reduction.

The invention claimed is:

1. A shaped catalyst body containing a mixed oxide of copper, zinc and aluminum, wherein
   the shaped catalyst body is present in an oxidized tablet form and contains calcium aluminate as binder material with a proportion by weight of calcium aluminate in the range from 5.0% to 30.0%, based on the shaped catalyst body; and
   the shaped catalyst body has a lateral compressive strength from 100 to 250 N.

2. The shaped catalyst body as claimed in claim 1, wherein the proportion by weight of calcium aluminate is in the range from 5.0% to 20.0%.

3. The shaped catalyst body as claimed in claim 1, having a fracture strength from 2 to 10%.

4. The shaped catalyst body as claimed in claim 1, having a lateral compressive strength after reduction and dry stabilization from 40 to 200 N.

5. The shaped catalyst body as claimed in claim 1, having a BET surface area in the range from 70 to 150 m$^2$/g and a pore volume, measured by mercury porosimetry, between 150 mm$^3$/g and 400 mm$^3$/g.

6. The shaped catalyst body as claimed in claim 1, having a copper surface area after reduction between 20 m$^2$/g and 50 m$^2$/g.

7. The shaped catalyst body as claimed in claim 1, having a proportion of pore volume made up by pores having a radius of from 7.0 to 40.0 nm between 50 and 95%.

8. The shaped catalyst body of claim 1, having
   a fracture strength from 2 to 10%;
   a lateral compressive strength after reduction and dry stabilization from 40 to 200 N;
   a BET surface area in the range from 70 to 150 m$^2$/g;
   a pore volume, measured by mercury porosimetry, between 150 mm$^3$/g and 400 mm$^3$/g;
   a copper surface area after reduction between 20 m$^2$/g and 50 m$^2$/g; and
   a proportion of pore volume made up by pores having a radius of from 7.0 to 40.0 nm between 50 and 95%.

9. The shaped catalyst body as claimed in claim 1, wherein the proportion by weight of calcium aluminate is in the range from 10.0% to 20.0%.

10. A process for producing the shaped catalyst body of claim 1, which comprises the following steps:
    a) mixing of a metal-containing mixture containing a mixed oxide of copper, zinc and aluminum with calcium aluminate and a lubricant,
    b) tableting of the mixture from step a) to give tableted shaped bodies, and
    c) thermal treatment of the tableted shaped bodies at a temperature between 100 and 500° C. for a time between 30 minutes and 4 hours to provide tableted shaped bodies present in an oxidic state and having a later compressive strength from 100 to 250 N.

11. The process as claimed in claim 10, wherein the metal-containing mixture is subjected to a thermal treatment in the range from 200 to 500° C., before step a).

12. The process as claimed in claim 10, wherein the metal-containing mixture is a mixed oxide of copper, zinc and aluminum.

13. The process as claimed in claim 10, wherein
    the mixture of step a) includes water, and
    the mixture is aged for a time of from 5 minutes to 10 hours before tableting.

14. The process as claimed in claim 10, wherein the thermal treatment takes place between 300° C. and 500° C. for a time between 1 hour and 3 hours.

15. A process for the synthesis of methanol from synthesis gas using the shaped catalyst body as claimed in claim 1.

16. A shaped catalyst body containing copper, zinc and aluminum and calcium aluminate as binder with a proportion by weight of the calcium aluminate of from 5.0% to 30.0%, based on the shaped catalyst body, the shaped catalyst body being produced by a process comprising:
    a) mixing of a metal-containing mixture containing a mixed oxide of copper, zinc and aluminum with calcium aluminate, a lubricant and water, and subjecting the mixture to an aging step,
    b) tableting of the mixture from step a) to give tableted shaped bodies, and
    c) thermal treatment of the tableted shaped bodies at a temperature between 100 and 500° C. for a time between 30 minutes and 4 hours to provide tableted shaped bodies present in an oxidic state and having a lateral compressive strength from 100 to 250 N.

17. A shaped catalyst body containing a mixed oxide of copper, zinc and aluminum, wherein
    the shaped catalyst body is present in tablet form and contains calcium aluminate as binder material with a proportion by weight of calcium aluminate in the range from 5.0% to 30.0%, based on the shaped catalyst body;
    the shaped catalyst body, when in an oxidized form, has a lateral compressive strength from 100 to 250 N; and
    the shaped catalyst body, when in a reduced form, has a lateral compressive strength from 40 to 200 N.

18. The shaped catalyst body as claimed in claim 17, wherein the proportion by weight of calcium aluminate is in the range from 5.0% to 20.0%.

19. The shaped catalyst body as claimed in claim 17, wherein the proportion by weight of calcium aluminate is in the range from 10.0% to 20.0%.

* * * * *